United States Patent [19]

Lachenberg

[11] Patent Number: 4,966,176
[45] Date of Patent: Oct. 30, 1990

[54] DENTAL FLOSSER

[76] Inventor: James A. Lachenberg, 508 Roberts Dr. - 2A, Glenwood, Ill. 60425

[21] Appl. No.: 288,631

[22] Filed: Dec. 22, 1988

[51] Int. Cl.⁵ .............................................. A61C 15/00
[52] U.S. Cl. ..................................................... 132/325
[58] Field of Search ............... 132/323, 324, 325, 326, 132/327

[56] References Cited

U.S. PATENT DOCUMENTS

| | | | |
|---|---|---|---|
| D. 245,713 | 9/1977 | Jennings | 132/323 |
| 0,618,009 | 1/1899 | La Varre | 132/325 |
| 1,640,607 | 8/1927 | Kitley | 132/325 |
| 2,047,456 | 7/1936 | Barsch | 132/326 |
| 2,381,530 | 8/1945 | Dembenski | 132/325 |
| 3,592,203 | 7/1971 | Johnson | 132/323 |
| 3,861,406 | 1/1975 | Stitt | 132/325 |
| 3,939,853 | 2/1976 | Spanondis | 132/323 |
| 3,993,085 | 11/1975 | Skinner | 132/325 |
| 4,458,702 | 7/1984 | Grollimuno | 132/322 |
| 4,518,000 | 5/1985 | Leverette | 132/325 |
| 4,574,823 | 3/1986 | Uriss | 132/325 |
| 4,637,412 | 1/1987 | Martinez | 132/323 |

*Primary Examiner*—Gene Mancene
*Assistant Examiner*—Adriene B. Lepiane
*Attorney, Agent, or Firm*—Kinzer, Plyer, Dorn, McEachran & Jambor

[57] ABSTRACT

This is concerned with a dental flossing mechanism in the nature of a hand tool which enables the user to easily floss his teeth, to easily change the floss between flossing operations, to easily install a new spool of floss as each spool is exhausted and to maintain a taut section of floss between arms while flossing is taking place primarily due to a novel floating axle floss spool with a ratchet mechanism effect.

3 Claims, 1 Drawing Sheet

U.S. Patent    Oct. 30, 1990    4,966,176
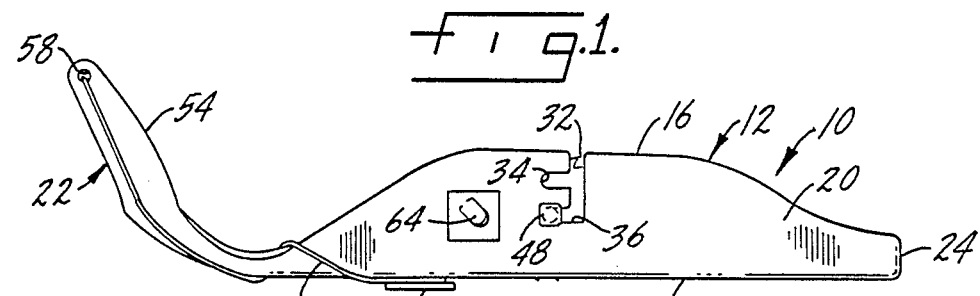
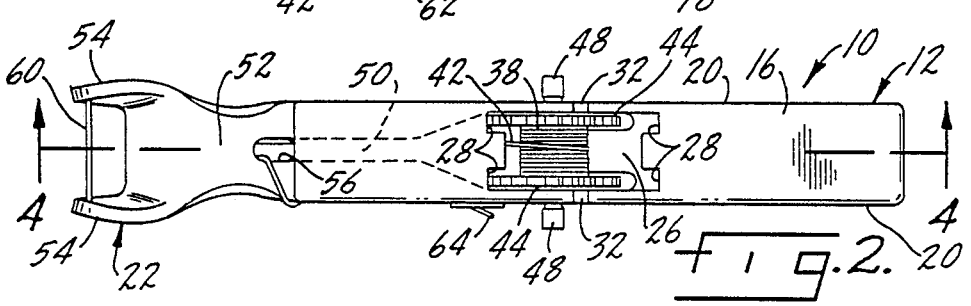
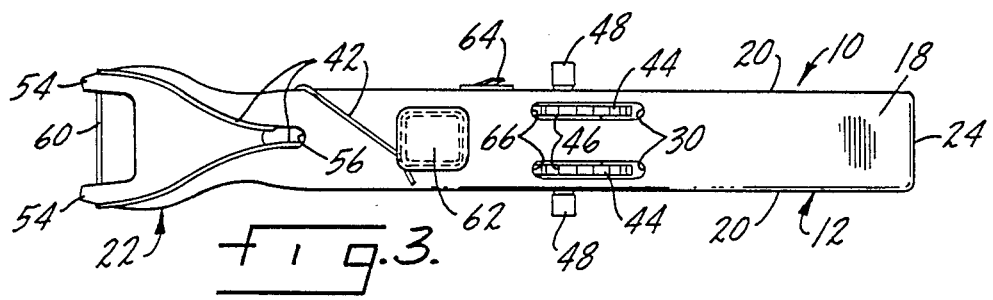
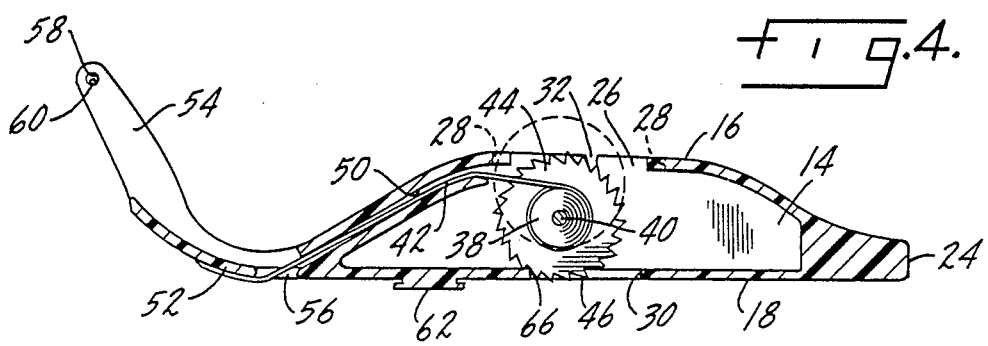
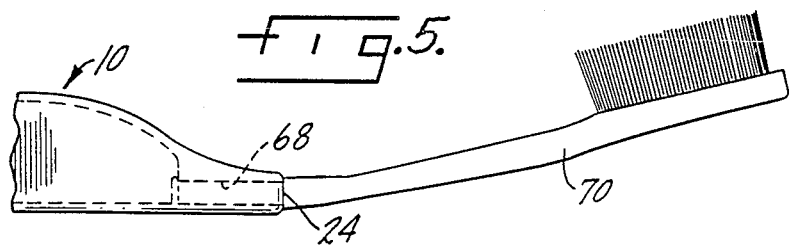

DENTAL FLOSSER

SUMMARY OF THE INVENTION

This invention is concerned with a hand flossing tool which is to say a tool that may be used in the bathroom or otherwise by an individual to floss their teeth. Floss is paid out from a spool with trunnions that act as a floating axle which mounts in the body of the device and extends through forked arms with an arrangement for tensioning it so that a free length of floss may be effected during flossing. The floss may also be paid out and cut off so that new and fresh sections of floss can be made immediately available in accordance with recommended flossing techniques.

A primary object of the invention is a new and improved flossing tool which keeps the floss taut in a simplified manner.

Another object is a flossing tool that eliminates the need of inserting dental floss into the mouth with the user's fingers.

Another object is a tool of the above type that eliminates the difficulty and awkwardness when flossing with the fingers.

Another object is a simplified, easy and convenient flossing device that will ensure usage.

Another object is a flossing device of the above type that does not require threading each time it is used.

Another object is a flossing device that enables the user to floss their teeth that is easy and comfortable and has added convenience.

Another object is a toothbrush attachment or other dental attachment such as a stimulator, mirror, plaque remover, etc. which may be attached to or combined with the flossing device.

Another object is a flossing device that uses a throw away floss spool but still eliminates the need to rethread after each use.

Another object is a specific floss spool with trunnions that act as a floating axle which also has gear type edges which allows for easy feeding but at the same time will tighten with a ratchet type action so that the floss is held tight during use.

Another object is a floss spool which creates an easier grip when tightening the floss line.

Another object is a mounting for a floss spool in a floss device of the above type that holds the floss spool stationary in one position and allows it to turn in another with automatic movement between the two by the use of a floating axle.

Other objects will appear from time to time in the ensuing specification.

BRIEF DESCRIPTION OF THE DRAWINGS

FIG. 1 is a side view of the flossing tool.
FIG. 2 is a top view of the flossing tool.
FIG. 3 is a bottom view of the flossing tool.
FIG. 4 is a section along line 4—4 of FIG. 2; and
FIG. 5 is a side view of a modification or attachment.

DETAILED DESCRIPTION OF THE PREFERRED EMBODIMENT

In FIGS. 1 through 3, the body of the unit is indicated generally at 10 and may be considered to be or have a somewhat central elongated body or housing 12 suitably shaped on the outside to be readily grasped by the hand of the user. As shown generally in FIG. 4, it may be considered to be generally hollow or open on the inside as at 14 to thereby provide a central cavity or recess or chamber for purposes explained hereinafter. The body unit has a top wall 16, a bottom wall 18 and more or less identical side walls 20. One end of the body or housing extends out to or is shaped in to an operative portion 22, explained more fully hereinafter, while the other end may be snubbed, cut off or could be an inlet for any number of attachments (i.e. toothbrush, stimulator, mirror, plaque remover, etc.) as at 24.

The top wall 16 of the body or housing has an opening 26 of a suitable size as explained later which may have a closing cover, not shown, and which is shaped at each end as at 28 into suitable recesses or the like for reasons explained hereinafter. The bottom wall 18 of the housing or body unit is shown with a pair of elongated slots or openings 30. The side walls 20 of the body or housing have channels 32 which open through the top wall and which connect to the top opening 26. The channels 32 have offsets 34 and 36 which are generally parallel to each other, spaced somewhat and function as set forth hereinafter.

A spool of floss 38 is shown in the body or cavity and may be assumed to have a central cylindrical portion or drum 40 for a suitable supply of floss 42 and flanges 44 on each end, each of which may have serrations or teeth or ratchet edges as indicated at 46 in FIG. 4. The central drum may be considered to have trunnions 48 which extend axially from each end and are of a size to fit down in the channels 32 and also to fit in and be received by the offsets 34 and 36.

The floss supply or spool is of a size so that it may be inserted down in the top opening 26 of the cavity with the trunnions acting as a floating axle, fitting in the channels 32, the flanges passing through the offsets or extensions 28. The user or operator may then position the trunnions or floating axle 48 in either the upper offset 34 or the lower 36 as explained hereinafter.

The front end of the body or cavity has a channel 50. With the spool fitted down in the cavity and located in the upper offset 34, the floss 42 may be threaded through the front channel 50 and automatically through an opening 56. When pulled by the user from below, the spool will rotate and the trunnions will also rotate in the channel offset 34.

The front end or extension 22 of the body member has a forklike appearance at 52 rising slightly upwardly to a pair of forked arms or extensions 54. The forklike portion 52 may have a suitable opening 56. The free end of the floss is then looped up and passed through opposed openings 58 at or toward the ends of the forked arms so that a free span of floss 60 is available. The free end of the floss is then passed back down through opening 56 and then extended to and wrapped around a suitable dead end 62. A cut off or knife edge 64 may be positioned on either one side or the other of the housing.

The openings or channels 30 in the bottom wall 18 of the housing are spaced so that, as shown in FIG. 3, they will receive the spool flanges. When the floating axle or trunnions of the spool are in the bottom offsets 36, the flanges are such that they will contact the front edges 66 of the slots 30 to effect a ratcheting or stop action as explained hereinafter.

The snubbed end 24 of the housing or handle unit may have a suitable socket 68 as shown in FIG. 5 so that an implement, such as a toothbrush, stimulator, plaque remover, mirror, etc., 70 may be suitably socketed therein and the unit used as such in a conventional manner.

The use, operation and function of the invention are as follows.

A spool of floss with its floating axle and flanged edges may be lowered into the cavity with the spool's trunnions acting as a floating axle, fitting down in the channels 32 and then slid into the upper recess 34 where the spool will freely rotate. The free end of the floss may be fed through the front channel 50, through the center opening 56, between the fingers through openings 58, back through the center opening 56 again, and then extended until it reaches and is wrapped around the dead end 62 with possibly some excess. At this point, the user may back the spool with its floating axle or trunnions out of the upper slot 34 and drop it down to the lower slot 36 where the spool flanges will enter the elongated slots 30.

It will be noted in FIG. 4 that when the spool is in the bottom slots 36, the flanges extend down into the channels 30 in the lower surface and also the upper portion of the flanges rise slightly above or through the top opening 26. Thus the user can reverse rotate the spool — clockwise in FIG. 4 — by passing his finger from left to right across the top opening in FIG. 4 thereby reverse winding the floss and when it is taut, it will remain so because the ratchet teeth will bear against stop surface 66. Thus, clockwise rotation of the spool ensures a taut span 60 and a positive lock. The ratchet teeth 46 take on the character of gear edges which serve two functions, first, causing the spool to lock against the forward surfaces 66 thereby maintaining the floss tight or tensioned and, second, it creates an easier grip when tightening the floss line. Although not shown, the surface 66 may be movable to cause a locking and releasing action against the spool flanges. After months of use or whenever the floss on one spool has been exhausted, the spool can be easily changed and a new full unit inserted which eliminates the need to rethread after each use. After each flossing, the floss line may be advanced somewhat so that a new span 60 is presented. The user may retighten the line by clockwise rotation of the spool, i.e. rubbing a finger from left to right in the top opening. The portion of the used floss beyond the dead end or protruding tab 62 may be cut off by the floss cutter 64 which eliminates the possibility of having any residue build up.

The unit has the advantage that you do not have to thread the unit after each use. A floss spool with its floating axle and geared edges may hold a substantial amount of floss line, for example on the order of 15 yards, i.e. about 540 inches, which, with about 6" being used per day, would mean that a floss spool would last something on the order of 90 days or 3 months. But these are merely examples. Another advantage is that the tension of the floss line is easily achieved with the gear type edges on the flanges which also holds the tension factor with an adequate amount of pressure resistance which eliminates the ineffectiveness other dental flossers experience when trying to keep a constant or consistent tension on the floss line.

The unit additionally provides an easy hand grip with the flexibility to reach all upper and lower teeth. The unit also does not require or contain any complicated mechanisms such as springs, key ways, sockets, tension bars, etc., which can create manufacturing difficulties and failures in use. In addition, the floss spools can be easily and quickly changed without the necessity of taking anything apart, dismantling the unit, etc. The unit has the advantage that flossing may be accomplished without the user having to insert his fingers and it also eliminates the difficulty and awkwardness realized when flossing. The difficulty of flossing with your fingers has discouraged many individuals and has held down or discontinued flossing. The present unit is a simplified, easy, and convenient means of flossing which will encourage and facilitate the performance of this task thereby reducing and/or preventing dental and periodontal problems and disease.

While in FIG. 5 I have shown a toothbrush as the inserted attachment, it should be understood that it could be any one of a number of other attachments, such as a stimulator, a mirror, a plaque remover, etc. In fact, the socket and attachments could be arranged so that a number or grouping of auxiliary devices could be supplied thereby giving the user several options.

While the preferred form and several variations of the invention have been shown and suggested, it should be understood that suitable additional modifications, changes, substitutions and alterations may be made without departing from the invention's fundamental theme.

The embodiments of the invention in which an exclusive property or privilege is claimed are defined as follows:

1. In a dental floss applicator for holding and applying dental floss between the teeth of a user in a dental floss operation, a generally longitudinally elongated handle body shaped to fit the hand of a user, an extended portion at one end having forked laterally spaced opposed arms, laterally opposed openings in the arms through which the dental floss extends in a direction lateral to the handle body, a dead end on the handle body around which the free end of the floss may be wrapped and snubbed after passing through the opposed openings in the arms, a cavity in the handle body with opposed lateral side walls, an opening in a top wall of the handle body to admit a spool of floss into the cavity, opposed lateral slots in the side walls of the cavity opening in the opening and having two pairs of opposed spaced forwardly directed offsets in the side walls, one pair of offsets being more remote from the opening than the other pair, a flanged spool of dental floss with an trunnions and trunnions thereon acting as a floating axle thereof in the cavity for paying out floss to the opposed openings in the arms, the axle freely fitting in the other pair of offsets to allow the spool to freely turn during threading of the floss to and between the forked arms, and a ratchet mechanism between at least one of the spool flanges and the handle body operative only when the trunnions are in the said one pair of offsets to automatically and releasably tension the floss and hold the spool against rotation after the user has secured the floss on the dead end when the trunnions of the spool are in the said one pair of offsets.

2. The structure of claim 1 further characterized in that the ratchet mechanism is responsive to the longitudinal forward movement of the spool so that movement of the spool tends to lock the ratchet mechanism while rearward movement in the other direction tends to release it.

3. The structure of claim 2 further characterized in that the ratchet mechanism includes generally parallel openings through the side of the cavity in the handle body opposite the spool receiving opening, and further including serrated teeth on the spool flanges which engage and lock against the ends of the openings.

* * * * *